United States Patent [19]

Sanagi

[11] Patent Number: 4,946,442
[45] Date of Patent: Aug. 7, 1990

[54] ENDOSCOPE TREATMENT DEVICE

[75] Inventor: Kenichiro Sanagi, Tokyo, Japan

[73] Assignee: Olympus Optical Co., Ltd., Japan

[21] Appl. No.: 344,100

[22] Filed: Apr. 26, 1989

Related U.S. Application Data

[62] Division of Ser. No. 875,714, Jun. 18, 1986, Pat. No. 4,857,057.

[30] Foreign Application Priority Data

Jun. 28, 1985 [JP] Japan .............................. 60-142183
Aug. 9, 1985 [JP] Japan .............................. 60-175508

[51] Int. Cl.$^5$ ............................................. A61M 5/18
[52] U.S. Cl. ................................................. 604/164
[58] Field of Search .............. 604/164, 165, 163, 158, 604/280

[56] References Cited

U.S. PATENT DOCUMENTS 4,136,695 1/1979 Dafoe .............................. 604/165 X
4,488,545 12/1984 Shen .................................. 604/165
4,668,226 5/1987 Omata et al. ...................... 604/164

Primary Examiner—John D. Yasko

[57] ABSTRACT

A structure of a treatment device to be inserted in the channel of an endoscope is disclosed. The treatment device includes a flexible elongated member, a treatment section having a sharp end portion, and a flexible outer tube for receiving the flexible elongated member and the treatment section to be movable forward/backward. A regulating member is mounted on the distal end portion of the outer tube. An abutting portion is formed inside the outer tube adjacent to the proximal end portion of the regulating member. The abutting portion is engaged with a shoulder portion formed on the treatment section in order to regulate the projecting amount of the treatment section. When the outer tube and the elongated member have a bending tendency, the sharp end portion of the treatment section is located on the inner side of the curve in the elongated member.

3 Claims, 4 Drawing Sheets

ENDOSCOPE TREATMENT DEVICE

This is a division of application Ser. No. 06/875,714, filed June 18, 1986, now U.S. Pat. No. 4,857,057.

The present invention relates to an endoscope treatment device which is inserted in a body cavity through a channel in an endoscope inserted in the body cavity and, more particularly, to a syringe device for directly injecting a drug solution into a diseased portion in the body cavity.

A treatment method is known wherein, when a drug solution is directly injected into a diseased portion in a body cavity, the distal end of the syringe device is inserted in the body cavity through a channel in an endoscope inserted in the body cavity. A syringe device used for this treatment has an outer tube capable of being inserted in the channel of the endoscope, an injection tube inserted in the outer tube which is capable of moving forward/backward, and a cannula attached to the distal end of the injection tube.

It is dangerous to project the distal end of the cannula from the distal end of the outer tube further than is necessary, since the tip of the cannula may injure the body cavity wall. For this reason, according to the conventional treatment method, a metal stop ring is mounted at the distal end of the injection tube to regulate the projecting length of the cannula, and a shoulder portion of the cannula abuts against the stop ring, thereby regulating the projecting length of the cannula, as disclosed in Japanese Utility Model Disclosure (Kokai) No. 57-126201.

With the conventional syringe device described above, however, the stop ring may fall off the injection tube when the shoulder portion of the cannula abuts against the stop ring strongly. It is dangerous if the stop ring falls off in the body cavity. This is because the body cavity wall may be hurt if the stop ring is left there or if the cannula projects from the distal end of the outer tube more than is necessary.

The injection and outer tubes of a conventional endoscope syringe device are formed by cutting an elongated tube member into predetermined lengths. When the tube member is stored or transported, it is rolled up since it is an elongated member. The tube member thus has a tendency to bend. Therefore, if the tube member with the bending tendency is cut and the cannula is mounted on the distal end of the injection tube without any particular attention being paid, the tip of the cannula may stick in or damage the inner surface of the outer tube.

In order to prevent this, a series of preparations must be performed in advance before performing treatment. The tube material must be corrected to be linear, correcting its bending tendency. However, this is uneconomical since it is laborious and costly.

SUMMARY OF THE INVENTION

It is an object of the present invention to provide an endoscope treatment device having a comparatively simple configuration, with high safety and operability.

It is another object of the present invention to provide an endoscope treatment device wherein a regulating member thereof mounted for regulating the projecting length of a cannula as the treatment device is prevented from falling off.

It is still another object of the present invention to provide an endoscope treatment device wherein, even if an outer tube and an elongated member inserted therein have a tendency to bend, the elongated member can be inserted in the outer tube without causing it to catch the biased sharp point of the cannula.

In order to achieve the above objects, the endoscope treatment device according to the present invention comprises: an elongated flexible member; a treatment section mounted at the distal end of the elongated flexible member and having a sharp distal end portion; an outer tube through which the treatment section and the elongated member are inserted to be movable forward/backward; and a regulating member mounted on an outer surface of a distal end portion of the outer tube, wherein an abutting portion is formed inside the outer tube adjacent to a proximal end portion of the regulating member, the abutting portion has an inner diameter smaller than that of a remaining portion of the outer tube, and a shoulder portion of the treatment section abuts against the abutting portion in order to regulate a projecting amount of the cannula.

An endoscope treatment device of the present invention comprises: a flexible outer tube having a bending tendency; an elongated member having a bending tendency and inserted in the outer tube to be movable forward/backward; and a treatment section mounted at a distal end of the elongated member, wherein the treatment section comprises a sharp end portion, and the sharp end portion is located closer to an inner side of a curve of the elongated member.

DETAILED DESCRIPTION OF THE PREFERRED EMBODIMENTS

Figure 1:
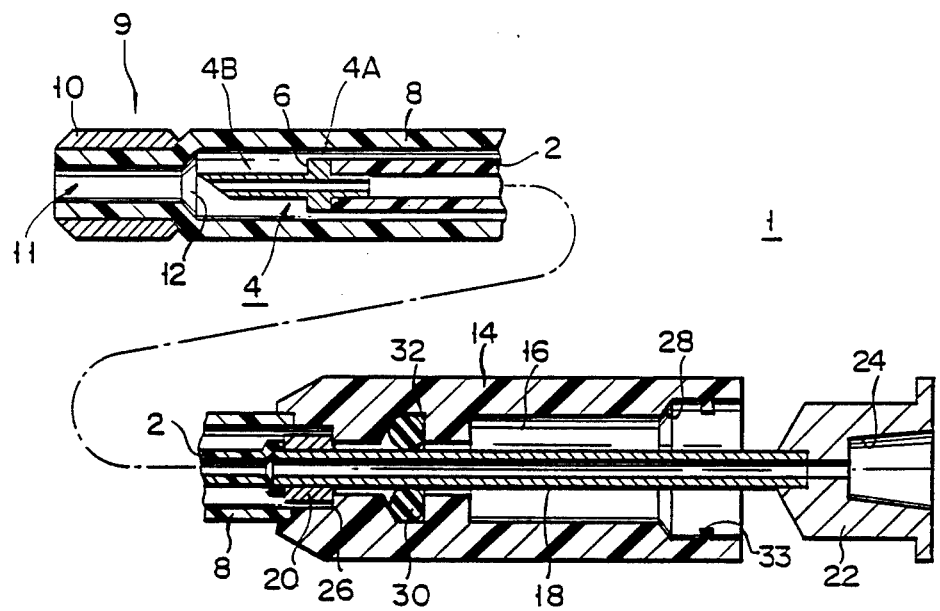
FIG. 1 is a schematic side sectional view of part of an endoscope treatment device according to an embodiment of the present invention.

An embodiment of the present invention will be described with reference to FIG. 1. Tubular cannula 4 is mounted at the distal end of flexible injection tube 2 made of a synthetic resin such as Teflon. Cannula 4 has a hollow cannula portion 4B. projecting from proximal end portion 4A thereof. Portion 4B has an outer diameter smaller than the outer diameter of injection tube 2. Proximal end portion 4A of cannula 4 has shoulder portion 6. Cannula 4 and injection tube 2 are inserted in flexible outer tube 8, made of a synthetic resin such as Teflon, to be movable forward/backward. Narrow portion 11, having an inner diameter considerably larger than the outer diameter of cannula portion 4B and smaller than the outer diameter of portion 4A, is formed at distal end portion 9 of tube 8. Regulating member 10 made of a metal pipe is fitted on the outer surface of the distal end portion of tube 8, and is adhered thereto. Abutting portion 12 having an inclined or curved portion is formed between narrow portion 11 and other portions of tube 8 excluding its distal end portion. The inner diameter of portion 12 is larger than that of portion 11 so that cannula 4 ca be inserted in abutting portion 12. Therefore, when cannula portion 4B is moved forward through narrow portion 11, shoulder portion 6 of cannula 4 abuts against portion 12, and the projecting length of cannular portion 4B from the distal end of tube 8 is thus regulated. Narrow portion 11 of tube 8 can have an inner diameter smaller than those of other portions thereof. Alternately, regulating member 10 can be mounted to elastically deform tube 8.

Cylindrical holder 14 is fixedly mounted on the proximal end portion of tube 8. Pipe 18 has an end connected to the proximal end of tube 2 and is inserted in path 16 formed in holder 14. Ring-like stopper 20 is mounted on the distal end portion of pipe 18. Metal piece 22 is connected to the proximal end of pipe 18. Connection port 24 for connecting a syringe (not shown) such as a syringe barrel is formed on metal piece 22. First engaging portion 26 is formed in path 16 of holder 14, closer to the distal end of path 16. First engaging portion 26 is engaged with stopper 20 to prevent detachment of tube 2. Second engaging portion 28 is formed in path 16, closer to its proximal end. Tube 2 is prevented from moving forward in the outer tube, when second engaging portion 28 is engaged with the distal end of metal piece 22. When cannula 4 is moved to the narrow portion 11, shoulder portion 6 of cannula 4 is engaged with abutting portion 12, and metal piece 22 is engaged with second engaging portion 28. Therefore, when metal piece 22 is urged inward until its distal end abuts against second engaging portion 28, tube 2 is elastically compressed. Cannula portion 4B is kept projecting from outer tube 8 by the elastic restoration force of tube 2.

An annular recess 32 is formed in the intermediate portion of holder 14. Elastic member 30 like an O-ring is in tight contact with pipe 18 and is held in recess 32. Projection 33 is formed on the inner surface of holder 14, the inner surface defining path 16 near the proximal end portion thereof. Projection 33 can be elastically urged into contact with outer surface of metal piece 22, thereby keeping metal piece 22 in the push-in position.

In the endoscope syringe device having the above structure, cannula portion 4B is withdrawn into outer tube 8. Tube 8 is then inserted in a channel (not shown) of the endoscope inserted in the body cavity, thus being guided into the body cavity. In this case, cannula portion 4B is housed in outer tube 8. Therefore, cannula portion 4B does not damage the channel of the endoscope or the body cavity wall. The distal end of tube 8 is moved close to a target position, and thereafter, metal piece 22 is moved forward by manual operation. As a result, cannula 4 is pushed through tube 2 until shoulder portion 6 abuts against abutting portion 12 of tube 8. Cannula portion 4B of cannula 4 then projects through narrow portion 11 by a predetermined length. In this state, when metal piece 22 is further pushed, tube 2 is elastically compressed within tube 8. The outer surface of metal piece 22 abuts against second engaging portion 28 with pushing projection 33, thereby preventing backward movement of metal piece 22. As a result, the projecting state of cannula portion 4B is securely maintained.

Even if shoulder portion 6 of cannula 4 abuts against abutting portion 12 of tube 8 strongly, it does not cause regulating member 10 to fall off tube 8. This is because regulating member 10 is mounted on the outer surface of tube 8 and abutting portion 12 is formed on the inner surface thereof, so that shoulder portion 6 does not abut directly against regulating member 10.

Figure 2:
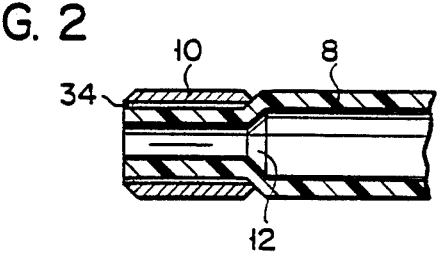
FIG. 2 is a side sectional view of a first modification of the distal end of the endoscope treatment device in FIG. 1.

FIG. 2 shows a first modification of the distal end portion of the treatment device of the present invention. In FIG. 2, adhesive 34 is filled between regulating member 10 and outer tube 8, and member 10 is securedly mounted on the outer surface of the distal end of tube 8.

Figure 3:
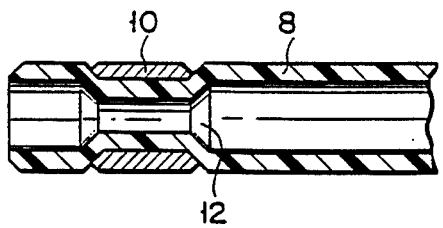
FIG. 3 is a side sectional view of a second modification of the distal end of the device in FIG. 1.

FIG. 3 shows a second modification of the distal end portion of the treatment device of the present invention. A portion of outer tube 8, which is separated from the distal end face of the distal end portion of tube 8 by a predetermined distance, is preformed by molding in order to form abutting portion 12. Regulating member 10 is then mounted on the molded portion of tube 8.

Figure 4:
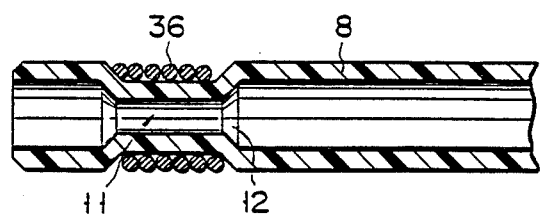
FIGS. 4 and 5 are respectively side sectional views of a third modification of the distal end of the device in FIG. 1.
Figure 5:
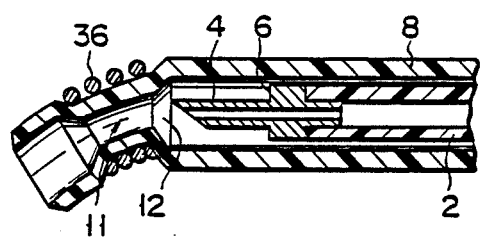

FIGS. 4 and 5 show a third modification of the distal end portion of the treatment device of the present invention. In FIGS. 4 and 5, in the same manner as the second modification, abutting portion 12 is formed at a position separated from the distal end face of outer tube 8 by a predetermined distance, and coil 36 is mounted as a regulating member on narrow portion 11. This structure can be smoothly inserted in the channel of a bent endoscope since coil 36 can be bent.

Figure 6:
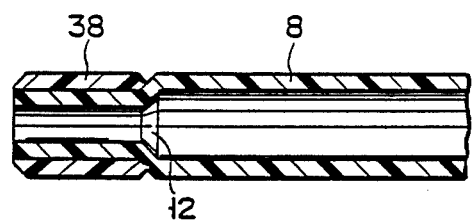
FIG. 6 is a side sectional view of a fourth modification of the distal end of the device in FIG. 1.

FIG. 6 shows a fourth modification of the distal end portion of the treatment device of the present invention. In FIG. 6, the regulating member is flexible tube 38 such as a Teflon tube, is mounted on the outer surface of the distal end portion of outer tube 8, and is adhered thereto.

Figure 7:
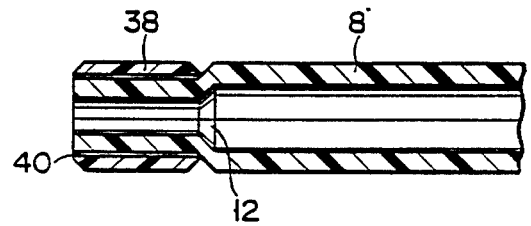
FIG. 7 is a side sectional view of a fifth modification of the distal end of the device in FIG. 1.

A fifth modification shown in FIG. 7 has substantially the same arrangement as the fourth modification, except that in FIG. 7, tube 38 is fixed on outer tube 8 with adhesive 40.

Figure 8:
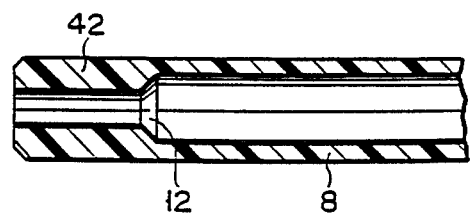
FIG. 8 is a side sectional view of a sixth modification of the distal end of the device in FIG. 1.

FIG. 8 shows a sixth modification of the distal end portion of the treatment device of the present invention. In FIG. 8, the distal end portion of outer tube 8 consists of only thick portion 42 serving as a regulating member. In this manner, an abutting portion having an inner diameter smaller than that of other portions is formed.

As described above in detail, the present invention provides an endoscope treatment device wherein a narrow portion is formed in the distal end portion of an outer tube, a regulating member is provided on the outer surface of the narrow portion, an abutting portion is formed between the narrow portion and the remaining portion, and the shoulder portion of a cannula abuts against the abutting portion. Since the cannula does not abut against the regulating member directly, the regulating member does not fall off the outer tube. In other words, the regulating member cannot be left in the body cavity, and the cannula cannot project further than is necessary, preventing damage to the body cavity wall. Therefore, the endoscope treatment device of the present invention has high safety.

Figure 9:
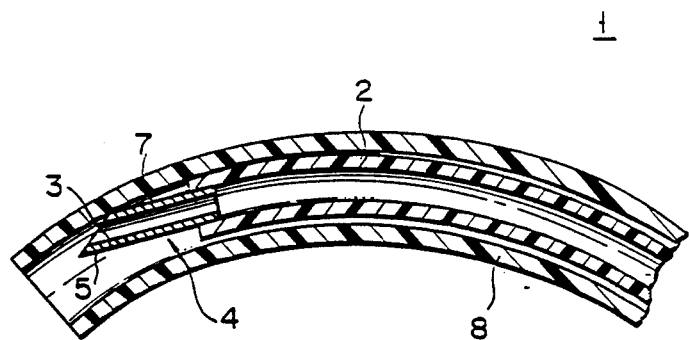
FIG. 9 is a side sectional view showing the distal end and its vicinity of an endoscope treatment device according to another embodiment of the present invention.
Figure 10:
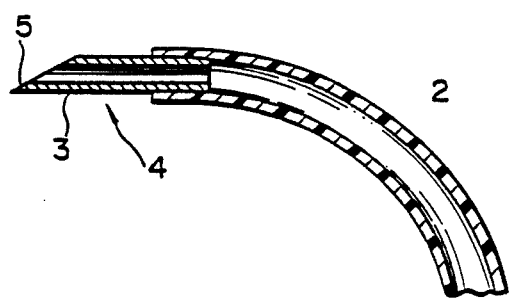
FIG. 10 is a side-sectional view showing an end portion of an injection tube in FIG. 9.
Figure 11:
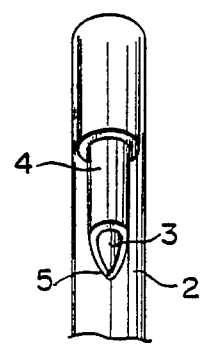
FIG. 11 is a front view of the injection tube and its vicinity in FIG. 10.

FIGS. 9 to 11 show another embodiment of the present invention. The endoscope treatment device disclosed in this embodiment has flexible outer tube 8 and flexible injection tube 2 inserted in tube 8 and capable of moving forward/backward. Both tubes 2 and 8 are made of a synthetic resin such as Teflon. Tubes 2 and 8 are rolled up during storage or transportation and thus have a tendency to bend in an arcuated manner. Cannula 4 is mounted on the distal end of tube 2. Cannula 4 is made of a rigid metal tube. Cannula tip 3 is formed by obliquely cutting the distal end portion of the rigid tube. Sharp point 5 of cannula tip 3 is located in tube 2 at an inner side of curved tube 2 This means that sharp point 5 of cannula 4 is located between an axis of tube 2 and the center of the radius of curvature thereof. Although sharp point 5 need not be located precisely on a line connecting the axis of tube 2 and the center of the radius of curvature thereof, it is preferably located in the vicinity of the line.

When injection tube 2 is inserted in outer tube 8, tube 2 is moved forward as it is guided by tube 8 along the curve thereof such that the curve of tube 8 coincides with that of tube 2, as shown in FIG. 9. As a result, sharp point 5 of cannula tip 3 located closer to the inner side of the curve of tube 2 is moved forward as it moves to the inner side of the curve. In other words, sharp point 5 is kept to be spaced apart from the inner surface of tube 8, as shown in FIG. 9. Therefore, even if cannula 4 contacts the inner surface of tube 8, it is only with belly 7 of cannula tip 3. Therefore, when tube 2 is inserted in tube 8, sharp point 5 of cannula 4 is not caught by or does not stick into the inner surface of tube 8. Sharp point 5 does not damage the inner surface of tube 8 or protrude therefrom. Furthermore, sharp point 5 can be inserted easily since the insertion resistance is small.

Even if the elongated flexible tube member has acquired a tendency to bend since it was rolled up during storage or transportation, with the above arrangement, the tube member with the bending tendency can be cut and used as a material for tubes 8 and 2. Therefore, the bending tendency of the tube member need not be corrected, thereby decreasing the manufacturing cost of syringe devices.

Figure 12:
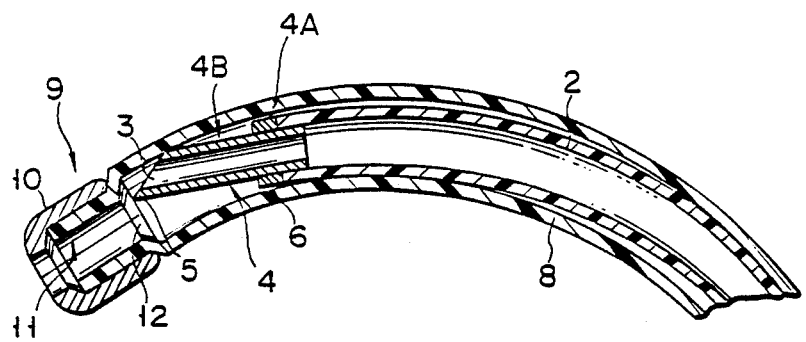
FIG. 12 is a side sectional view of a modification of the distal end portion of the endoscope treatment device of FIG. 9.

FIG. 12 shows a modification of the distal end portion of the endoscope treatment device in FIG. 9. In FIG. 12, narrow portion 11, having an inner diameter much larger than the outer diameter of cannula 4B and smaller than the outer diameter of proximal end portion 4A, is formed on the distal end portion of outer tube 9. Abutting portion 12 having an inclined or curved surface is formed between narrow portion 11 and the remaining portion of tube 8. Tubular regulating member 10 is fixedly mounted on the outer surface of the distal end portion having abutting portion 12. Shoulder portion 6 is formed by mounting a ring-like member in the vicinity of tube 2, i.e., on proximal end portion 4A of cannula 4. Shoulder portion 6 abuts against abutting portion 12. Therefore, when tube 2 is moved forward, the distal end of cannula portion 4B of cannula 4 projects from the opening in the distal end of outer tube 8 and shoulder portion 6 abuts against abutting portion 12, thereby regulating the projecting amount of cannula 4 to an adequate length.

Figure 13:
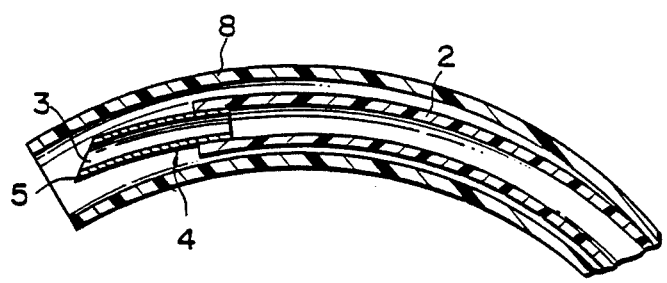
FIG. 13 is a side sectional view of another modification of the cannula of the endoscope treatment device in FIG. 9.

FIG. 13 shows another modification of the cannula shown in FIG. 9. In FIG. 13, cannula 4 is bent with substantially the same radius of curvature as injection tube 2, along the curve thereof. As a result, sharp point 5 of cannula tip 3 is spaced sufficiently apart from and located in the vicinity of the central portion of tube 8.

Figure 14:
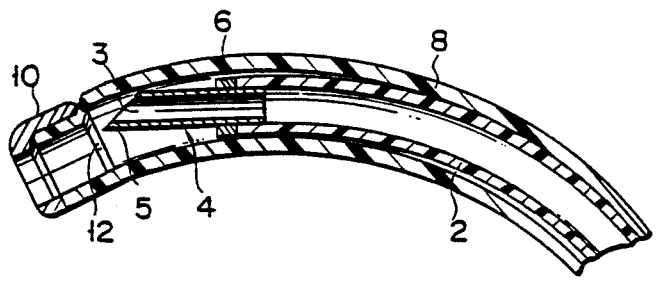
FIG. 14 is a side sectional view of still another modification of the distal end portion in FIG. 9.

FIG. 14 shows still another modification of the distal end portion of the endoscope treatment device in FIG. 9. In FIG. 14, abutting portion 12 shown in FIG. 12 is formed at only the outer side of the curve of outer tube 8, thereby preventing sharp point 5 of cannula tip 3 from being caught thereby. This is because no step projects from the inner side of the curve of tube 8, though which cannula tip 3 passes.

What is claimed is:

1. An endoscope treatment device to be slidably inserted in a channel of an endoscope comprising:
a flexible curved outer tube having a distal end portion, a center of curvature, an inner section having a radius of curvature measured from said center of curvature, an outer section having a radius of curvature measured from said center of curvature, said outer section radius of curvature being greater than said inner section radius of curvature, a distal end portion, an outside surface on said outer section, and an inner surface on said outer tube inner section and said outer tube outer section, said outer tube having an inner diameter defined by said inner surface;
an elongated curved member which is inserted in said outer tube to be movable forward/backward, said elongated curved member having a distal end portion, a center of curvature, an inner side having an inner radius of curvature extending from said elongated curved member center of curvature, and an outer side having an outer radius of curvature extending from said curved member center of curvature, said elongated curved member center of curvature and said flexible curved outer tube center of curvature being located proximate to each other so that said elongated curved member and said outer tube are congruent with each other adjacent to said distal end portions of each, said elongated curved member having an axis located between said elongated curved member inner section and said elongated curved member outer section;
a treatment section having a distal end and a proximal end and being mounted at said treatment section proximal end on the distal end portion of said elongated curved member, said treatment section having an outer wall located adjacent to the outer wall inner surface of said elongated curved member outer wall and an inner wall having a sharp point at said distal end thereof, said sharp point being located between said elongated curved member axis and said elongated curved member center of curvature and being located between said elongated curved member axis and the inner surface of said elongated curved member inner wall, and a shoulder portion formed on said treatment section proximal end;
a regulating member mounted on said outer tube outside surface near said outer tube distal end portion and surrounding said outer tube and having a distal end and a proximal end; and an abutting portion formed on said outer tube inner surface adjacent to said regulating member proximal end, said abutting portion having an inner diameter which is smaller than said outer tube inner diameter and which is located to be engaged with said treatment section shoulder portion to regulate the amount of said treatment section which projects out of said outer tube through said outer tube distal end portion.

2. A device according to claim 1, wherein said treatment section is bent to coincide with the curve of said elongated member.

3. A device according to claim 1, wherein said abutting portion is formed at only the outer side of the curve in said outer tube.

* * * * *